United States Patent
Gebert-Schwarzwaelder et al.

(10) Patent No.: US 10,251,826 B2
(45) Date of Patent: Apr. 9, 2019

(54) ALKALINE AGENT FOR LIGHTENING HAIR CONTAINING OXIDANTS AND SPECIAL CARBOXYLIC ACID ESTERS

(71) Applicant: Henkel AG & Co. KGaA, Duesseldorf (DE)

(72) Inventors: Antje Gebert-Schwarzwaelder, Neuss (DE); Helmut Giesa, Meerbusch (DE); Astrid Kroos, Monheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/788,842

(22) Filed: Oct. 20, 2017

(65) Prior Publication Data
US 2018/0140523 A1    May 24, 2018

(30) Foreign Application Priority Data
Nov. 24, 2016   (DE) .................. 10 2016 223 333

(51) Int. Cl.
| | | |
|---|---|---|
| *A61K 8/37* | (2006.01) | |
| *A61K 8/22* | (2006.01) | |
| *A61K 8/23* | (2006.01) | |
| *A61K 8/25* | (2006.01) | |
| *A61Q 5/10* | (2006.01) | |
| *A61Q 5/08* | (2006.01) | |

(52) U.S. Cl.
CPC .................. *A61K 8/37* (2013.01); *A61K 8/22* (2013.01); *A61K 8/23* (2013.01); *A61K 8/25* (2013.01); *A61Q 5/10* (2013.01); *A61K 2800/31* (2013.01); *A61Q 5/08* (2013.01)

(58) Field of Classification Search
CPC ... A61K 8/22; A61K 8/37; A61Q 5/08; A61Q 5/06; A61Q 5/065
See application file for complete search history.

(56) References Cited

U.S. PATENT DOCUMENTS

| | | | | |
|---|---|---|---|---|
| 3,634,022 A | * | 1/1972 | Robbins ............... | A61K 8/8147 8/127.51 |
| 5,558,071 A | * | 9/1996 | Ward ................... | F02P 3/02 123/598 |
| 6,579,851 B2 | * | 6/2003 | Goeke .................. | A61K 38/26 514/11.7 |
| 8,461,129 B2 | * | 6/2013 | Bolduc ................ | A61L 15/28 127/49 |
| 2010/0000564 A1 | * | 1/2010 | Monda ................. | A61K 8/494 132/208 |
| 2011/0028412 A1 | * | 2/2011 | Cappello ............ | A61K 31/7004 514/25 |
| 2013/0041004 A1 | * | 2/2013 | Drager ................. | A61K 9/08 514/394 |
| 2013/0084243 A1 | * | 4/2013 | Goetsch ............. | C07K 16/2863 424/1.49 |
| 2013/0096073 A1 | * | 4/2013 | Sidelman ........... | A61K 38/1709 514/21.6 |

FOREIGN PATENT DOCUMENTS

WO    2012038334 A1    3/2012

OTHER PUBLICATIONS

Sodium Silicate (https://www.cosmeticsinfo.org/ingredient/sodium-silicate) availble online May 21, 2015, pp. 1-3 (Year: 2015).*
Intellectual Property Office, Search Report under Section 17(5) for United Kingdom Patent Application No. GB1717163.8 dated Jul. 4, 2018.

* cited by examiner

*Primary Examiner* — Andrew S Rosenthal
(74) *Attorney, Agent, or Firm* — Lorenz & Kopf, LLP

(57) ABSTRACT

The subject matter of the present disclosure includes agents for lightening keratin fibers, more particularly human hair, containing in a cosmetic carrier:
(a) at least one carboxylic acid ester of the formula (I)

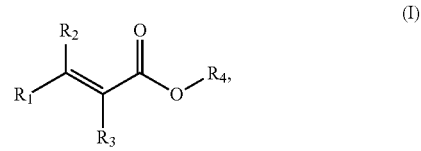

(b) at least one peroxide compound, and
(c) water,
wherein the agent has a pH value in the range of from about 7.5 to about 12.5.
A further subject matter of the present disclosure includes a kit-of-parts in which the aforementioned components exist packed separately in two agents (A) and (B).

20 Claims, No Drawings

ALKALINE AGENT FOR LIGHTENING HAIR CONTAINING OXIDANTS AND SPECIAL CARBOXYLIC ACID ESTERS

CROSS-REFERENCE TO RELATED APPLICATION

This application claims priority to German Patent Application No. 10 2016 223 333.5, filed Nov. 24, 2016, which is incorporated herein by reference in its entirety.

TECHNICAL FIELD

The present disclosure relates to the cosmetic sector. The subject matter of the present disclosure concerns agents for lightening keratin fibers, more particularly human hair, said agents containing in an anhydrous cosmetic carrier at least one peroxide compound and at least one keratin cross-linker of a special carboxylic acid ester type of a formula (I). These agents are set to an alkali pH value in the range of from about 7.5 to about 12.5.

A further subject matter of the present disclosure is a kit-of-parts which, packed separately from one another in two containers, including the agents (A) and (B), wherein agent (A) is an anhydrous agent containing, in addition to hydrogen peroxide, at least one carboxylic acid ester of the formula (I) and agent (B) is anhydrous and contains at least one persulfate. The mixture of agents (A) and (B) has a pH value in the range of from about 7.5 to about 12.5.

BACKGROUND

The problem with the oxidative coloring or blonding of hair is that aggressive agents can cause damage to the keratin fibers. More particularly, the natural hydrophobicity of the keratin fiber is reduced, since the dye and/or lightening agent first needs to make the hair penetrable in order to develop its effect. The water-repellent effect, however, is on the one hand a natural protection mechanism of the hair. On the other hand, parameters such as gloss, softness, hair strength, hold and "falling" of the hair desired by the consumer are closely associated therewith.

In order to overcome the stated disadvantages, the use of so-called keratin cross-linkers is known from the prior art. Keratin cross-linkers are unsaturated, monomeric compounds with a molecular mass of less than about 500 g/mol. When keratin cross-linkers are applied to hair, they are able to diffuse well into the hair fiber due to their small molecular mass. Inside the hair fiber, the keratin cross-linkers then form—either with the hair fiber itself or with other cross-linker molecules—adducts, said adduct formation occurring at the double bond of each cross-linker molecule.

Corresponding keratin cross-linkers are described, for example, in EP 2478892 A1. In chemical terms, this cross-linking is effectively the addition to a double bond. In order to activate the double bond of the keratin cross-linker, this is often located in close proximity of a group with strong electron-withdrawing properties (a carboxyl group, for example). The addition reaction can also be further facilitated by the use of initiators. In EP 2478892 A1, persulfates, peracids or azo compounds, for example, can also be used. In this context, an acid range of from about 4.0 to about 6.9 is described as the optimum pH value for this reaction.

In the works addressed by this application, however, it now transpires that the keratin cross-linkers described in EP 2478892 A1 are not optimally adapted to the blonding of keratin fibers.

The setting of an alkali pH value may be desirable to achieving a satisfactory blond effect. If the acid pH value proposed in EP 2478892 A1 is set, the blond effect may be too weak.

The present disclosure therefore addresses the problem of preparing an agent for the oxidative lightening and/or blonding of hair that causes no or minimal damage to the hair, yet still has a very strong lightening effect.

More particularly, the objective is to prepare lightning agents that have a strong blonding effect without the hair becoming fragile, dull or damaged in any other way. Despite the strong lightening effect, the hair fiber as a whole is to be stabilized. Moreover, the hair protection achieved should take the shortest time possible and occur, where possible, together with the dyeing and/or lightening step itself.

BRIEF SUMMARY

It has now been found that the aforementioned problem can be entirely solved by creating the lightening and/or blonding effect using an agent which, in an anhydrous cosmetic carrier, contains in addition to the obligatory peroxide compound, at least one special carboxylic acid ester of a formula (I) and has a pH value in the range of from about 7.5 to about 12.5.

A first subject matter of the present disclosure is an agent for lightening keratin fibers, more particularly human hair, containing in a cosmetic carrier:

(a) at least one carboxylic acid ester of the formula (I)

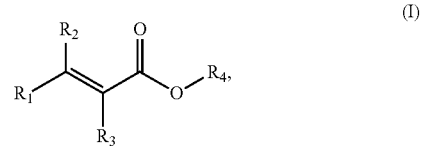

wherein $R_1$, $R_2$, $R_3$ denote independently a hydrogen atom, a $C_1$-$C_6$-alkyl group, a $C_2$-$C_6$-alkenyl group, a hydroxy-$C_1$-$C_6$-alkyl group, or a $C_1$-$C_6$-alkoxy carbonyl group, $R_4$ denotes a $C_1$-$C_6$-alkyl group, a $C_2$-$C_6$-alkenyl group or an aryl group, (b) at least one peroxide compound, and (c) water, wherein the agent has a pH value in the range of from about 7.5 to about 12.5.

It emerged that, after applying the agent as contemplated herein, less hair breakage occurred during the subsequent combing step and the stability of the fibers was higher. The increased fiber stability can be established by employing DSC (Difference Scanning Calorimetry) measurements, for example. Moreover, the hair lost less elasticity than after the application of blonding agents outside of the scope of the present disclosure. The elasticity of a hair fiber was able to be established through stress-strain measurements, for example.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The expression used in the present disclosure "lightening of keratin fibers" means, more particularly, a blonding or bleaching of the fibers. After the lightening agent has been applied, the treated keratin fiber is a lighter shade than before the lightening or blonding agent is applied. The degree of lightening can, for example, be quantified visually or also by colorimetric measurement of the hair strands (measurement of the Lab values). With the colorimetric measurement, the L-value denotes the lightness of a keratin fiber and/or hair strand (when L=100, the hair strand is white diffuse, when L=0, the hair strand is black). After the lightening agent as contemplated herein has been applied, the strand has a correspondingly higher L-value.

As used herein, the expression used in the invention "lightening of keratin fibers" also means a lightening coloring (or color-blonding). In this case, the agent can contain, in addition to the peroxide compound, dyes, though such dyes are contained only in small amounts to tint the lightening effect. After the dye-containing lightening agent has been applied, the treated keratin fiber is therefore a lighter shade than before the agent is applied. The agents as contemplated herein contain elements in an anhydrous cosmetic carrier. For the purpose of lightening (and/or lightening coloring), carriers such as creams, emulsions, gels or surfactant-containing, foaming solutions such as shampoos, foaming aerosols, foam formulations or other preparations suitable for application on the hair, are used.

As used herein, anhydrous-alcoholic solutions are, more particularly, anhydrous solutions containing from about 0.1 to about 70 percentage by weight of a $C_1$-$C_4$ alcohol, more particularly ethanol and/or isopropanol. The agents as contemplated herein can also contain other organic solvents, such as methoxybutanol, benzyl alcohol, ethyldiglycol or 1,2-propylene glycol. All water-soluble organic solvents are acceptable.

(a) Carboxylic Acid Ester of the Formula (I)

As the first component (a), the agent as contemplated herein for lightening the keratin fibers contains at least one carboxylic acid ester of the formula (I)

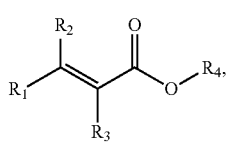

(I)

wherein $R_1$, $R_2$, $R_3$ denote independently a hydrogen atom, a $C_1$-$C_6$-alkyl group, a $C_2$-$C_6$-alkenyl group, a hydroxy-$C_1$-$C_6$-alkyl group, or a $C_1$-$C_6$-alkoxy carbonyl group, and $R_4$ denotes a $C_1$-$C_6$-alkyl group or a $C_2$-$C_6$-alkenyl group.

The keratin cross-linkers of the formula (I) are carboxylic acid esters. It emerged that these carboxylic acid esters also have an excellent substantivity to hair at alkali pH values.

Measurements, in which the effects of carboxylic acid esters were compared to the effect of the corresponding acids, demonstrated that better fiber protection can be achieved in an alkaline medium with the carboxylic acid esters than with carboxylic acids. Without being bound to this theory, it is believed that the corresponding acids are deprotonated at alkali pH values and hence negatively charged. As to those carboxylic acid cross-linkers outside the scope of this disclosure, this negative charge impedes their elevation to the keratin fibers, which are negatively charged to a greater or lesser degree depending on the amount of damage.

Examples of the substituents $R_1$, $R_2$, $R_3$ and $R_4$ stated in formula (I) are shown below: Examples of $C_1$-$C_6$-alkyl groups are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4CH_3$, —$(CH_2)_5CH_3$. In some embodiments, alkyl radicals are methyl and ethyl. Examples of $C_2$-$C_6$-alkenyl groups are vinyl, prop-2-enyl (allyl), 2-methyl-prop-2-enyl, but-3-enyl, but-2-enyl, pent-4-enyl or pent-3-enyl. Examples of $C_2$-$C_6$-hydroxyalkyl groups are —$CH_2$—$CH_2$—OH, —$CH_2$—$CH_2$—$CH_2$—OH, —$CH_2$—CH(OH)—$CH_3$, —$CH_2$—$CH_2$—$CH_2$—$CH_2$—OH, the —$CH_2$—$CH_2$—OH group being employed in an embodiment.

Examples of $C_1$-$C_6$-alkoxy-carbonyl groups are the methoxycarbonyl group (—C(O)OCH$_3$) or the ethoxycarbonyl group (—C(O)OCH$_2$CH$_3$). An example of an aryl group is a phenyl group.

In the case of the carboxylic acid ester of the formula (I), the radical $R_1$ can denote a hydrogen atom, a $C_1$-$C_6$-alkyl group, a $C_2$-$C_6$-alkenyl group, a hydroxy-$C_1$-$C_6$-alkyl group or a $C_1$-$C_6$-alkoxy-carbonyl group.

In this context, it emerged that suitable fiber protection could be achieved with the carboxylic acid esters of the formula (I), wherein $R_1$ denotes a $C_1$-$C_6$-alkyl group, which in particular embodiments may be a methyl group or an ethyl group.

In another embodiment, an agent for the lightening of keratin fibers as contemplated herein is exemplified in that it (a) contains at least one carboxylic acid ester of the formula (I), wherein $R_1$ denotes a $C_1$-$C_6$-alkyl group, for example a methyl group or an ethyl group.

In the case of the carboxylic acid ester of the formula (I), the radical $R_2$ can denote a hydrogen atom, a $C_1$-$C_6$-alkyl group, a $C_2$-$C_6$-alkenyl group, a hydroxy-$C_1$-$C_6$-alkyl group or a $C_1$-$C_6$-alkoxy-carbonyl group.

It also emerged that the carboxylic acid esters of the formula (I) are suitable for solving the problem addressed by the disclosure if the radical $R_2$ denotes a hydrogen atom.

In another embodiment, an agent for the lightening of keratin fibers as contemplated herein is exemplified in that it (a) contains at least one carboxylic acid ester of the formula (I), wherein $R_2$ denotes a hydrogen atom.

In the case of the carboxylic acid ester of the formula (I), the radical $R_3$ can denote a hydrogen atom, a $C_1$-$C_6$-alkyl group, a $C_2$-$C_6$-alkenyl group, a hydroxy-$C_1$-$C_6$-alkyl group or a $C_1$-$C_6$-alkoxy-carbonyl group.

It also emerged that the carboxylic acid esters of the formula (I) are suitable for solving the problem addressed by the disclosure if the radical $R_3$ denotes a hydrogen atom.

In another embodiment, an agent for the lightening of keratin fibers as contemplated herein is exemplified in that it (a) contains at least one carboxylic acid ester of the formula (I), wherein $R_3$ denotes a hydrogen atom.

In the case of carboxylic acid esters of the formula (I), radical $R_4$ can denote a $C_1$-$C_6$-alkyl group or a $C_2$-$C_6$-alkenyl group.

It also emerged that the carboxylic acid esters of the formula (I) are suitable for solving the problem addressed by the disclosure if the radical $R_4$ denotes a methyl group, an ethyl group, a n-propyl group (—$CH_2$—$CH_2$—$CH_3$) or a n-butyl group (—$CH_2$—$CH_2$—$CH_2$—$CH_3$).

In another embodiment, an agent for the lightening of keratin fibers as contemplated herein is exemplified in that it (a) contains at least one carboxylic acid ester of the formula (I), wherein $R_4$ denotes a methyl group, an ethyl group, a n-propyl group or a n-butyl group.

In other words, an agent for lightening keratin fibers, more particularly human hair, may contain in a cosmetic carrier (a) at least one carboxylic acid ester of the formula (I)

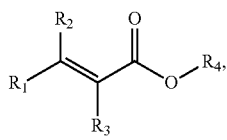
(I)

wherein $R_1$ denotes a $C_1$-$C_6$-alkyl group, $R_2$ denotes a hydrogen atom, $R_3$ denotes a hydrogen atom $R_4$ denotes a $C_1$-$C_6$-alkyl group and (b) at least one peroxide compound, and (c) water, wherein the agent has a pH value in the range of from about 7.5 to about 12.5.

Agents for lightening keratin fibers as contemplated herein, are exemplified in that they contain at least one carboxylic acid ester of the formula (I), which is selected from Methyl prop-2-enoate

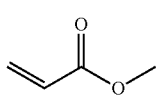

Ethyl prop-2-enoate

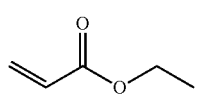

Propyl prop-2-enoate

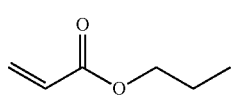

Phenyl prop-2-enoate

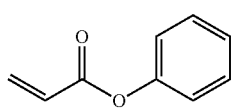

Methyl 2-methylprop-2-enoate

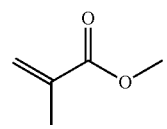

Ethyl 2-methylprop-2-enoate

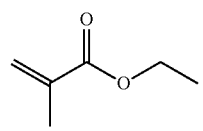

Propyl 2-methylprop-2-enoate

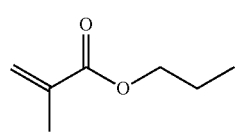

Phenyl 2-methylprop-2-enoate

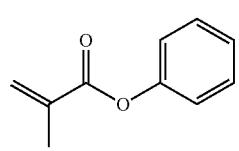

Methyl (E)-2-butenoate

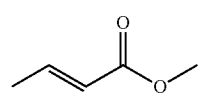

Ethyl (E)-2-butenoate

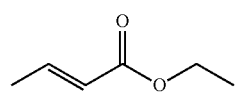

Propyl (E)-2-butenoate

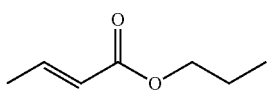

Phenyl (E)-2-butenoate

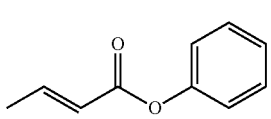

Methyl 3-methyl-2-butenoate

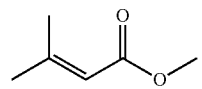

Ethyl 3-methyl-2-butenoate

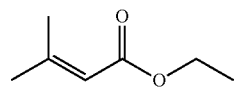

Propyl 3-methyl-2-butenoate

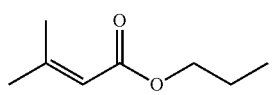

Phenyl 3-methyl-2-butenoate

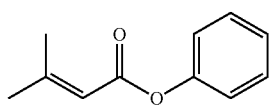

Methyl (E)-2-methyl-2-butenoate

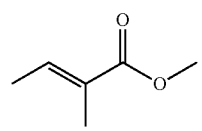

Ethyl (E)-2-methyl-2-butenoate

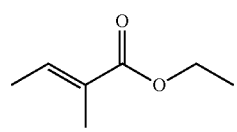

Propyl (E)-2-methyl-2-butenoate

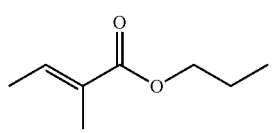

Phenyl (E)-2-methyl-2-butenoate

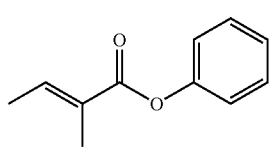

Methyl (Z)-2-methyl-2-butenoate

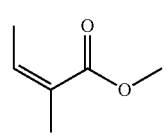

Ethyl (Z)-2-methyl-2-butenoate

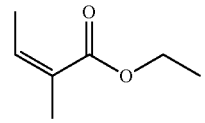

Propyl (Z)-2-methyl-2-butenoate

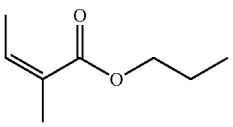

Phenyl (Z)-2-methyl-2-butenoate

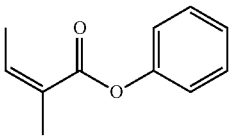

Methyl 2,3-dimethyl-2-butenoate

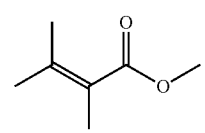

Ethyl 2,3-dimethyl-2-butenoate

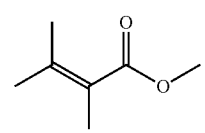

Propyl 2,3-dimethyl-2-butenoate

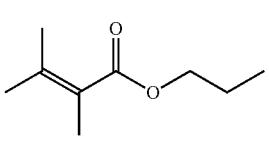

9

Phenyl 2,3-dimethyl-2-butenoate

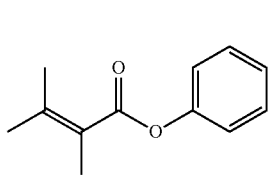

Methyl 2-methylbutanoate

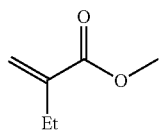

Ethyl 2-methylbutanoate

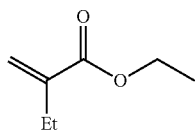

Propyl 2-methylbutanoate

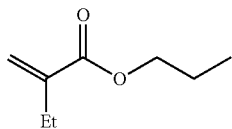

Phenyl 2-methylbutanoate

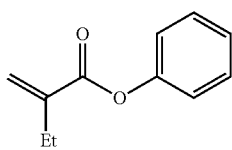

Methyl (E)-2-pentenoate

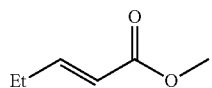

Ethyl (E)-2-pentenoate

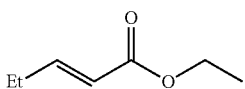

10

Phenyl (E)-2-pentenoate

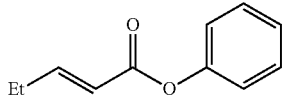 [SMILES: CC/C=C/C(=O)Oc1ccccc1]

Methyl (E)-3-methyl-2-pentenoate

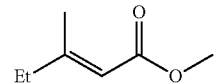

Ethyl (E)-3-methyl-2-pentenoate

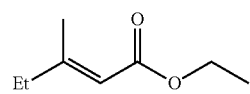

Phenyl (E)-3-methyl-2-pentenoate

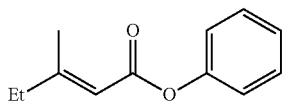

Methyl (E)-2-ethyl-2-butenoate

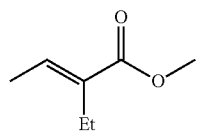

Ethyl (E)-2-ethyl-2-butenoate

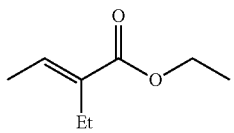

Phenyl (E)-2-ethyl-2-butenoate

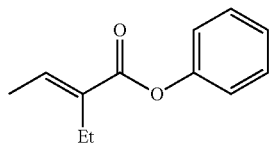

Methyl (E)-2,3-dimethyl-2-pentenoate

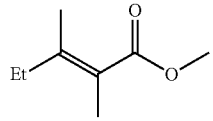

Ethyl (E)-2,3-dimethyl-2-pentenoate

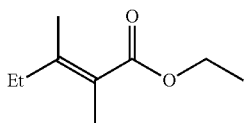

Phenyl (E)-2,3-dimethyl-2-pentenoate

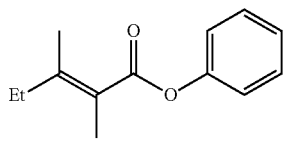

Methyl-2-ethyl-3-methyl-2-butenoate

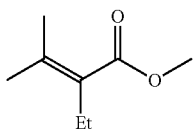

Ethyl-2-ethyl-3-methyl-2-butenoate and/or

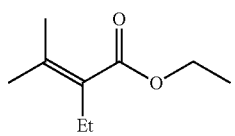

Phenyl-2-ethyl-3-methyl-2-butenoate

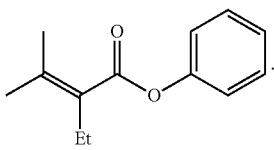

Within the aforementioned group of carboxylic acid esters of the formula (I), the compounds selected from the following, are once again reiterated
Methyl (E)-2-butenoate
Ethyl (E)-2-butenoate
Methyl (E)-2-pentenoate
Ethyl (E)-2-pentenoate To achieve optimum fiber protection, the agents as contemplated herein contain the carboxylic acid ester(s) of the formula (I), in specific quantity ranges. One embodiment is if the agent as contemplated herein contains—relative to the total weight thereof—(a) one or more carboxylic acid esters of the formula (I) in a total quantity of from about 0.1 to about 3.5 wt. %, for example from about 0.2 to about 2.4 wt. %, such as from about 0.3 to about 1.8 wt. % and in one embodiment from about 0.4 to about 1.2 wt. %.

In a further embodiment, an agent for lightening keratin fibers as contemplated herein is exemplified in that it contains—relative to the total weight thereof—(a) one or more carboxylic acid esters of the formula (I) in a total quantity of from about 0.1 to about 3.5 wt. %, for example from about 0.2 to about 2.4 wt. %, such as from about 0.3 to about 1.8 wt. % and in one embodiment from about 0.4 to about 1.2 wt. %.

(b) Peroxide Compound

The agent as contemplated herein is an agent for lightening (i.e. bleaching and/or color-blonding) keratin fibers, more particularly human hair. To achieve the lightening effect, the agent therefore contains at least one peroxide compound as the oxidant (b).

Hydrogen peroxide and persulfates (also referred to as peroxide sulfates) are commonly used as suitable peroxide compounds. Ammonium persulfate (ammonium peroxodisulfate), potassium persulfate (potassium peroxodisulfate) and sodium persulfate (sodium peroxodisulfate) are stated as suitable persulfates.

In a further embodiment, an agent for lightening keratin fibers as contemplated herein is exemplified in that it
(b) contains at least one peroxide compound from the group of hydrogen peroxide, ammonium peroxodisulfate, potassium peroxodisulfate and/or sodium peroxodisulfate.

Hydrogen peroxide is used either in the form of its anhydrous solution and/or in the form of its solid adducts to organic or inorganic compounds, such as urea, melamine and sodium borate. As an embodiment, hydrogen peroxide is used in the form of its anhydrous solution.

Preferably, the quantity of oxidants in the agent as contemplated herein is from about 0.5 to about 12 wt. %, such as from about 2 to about 10 wt. %, for example from about 3 to about 9 wt. % (calculated as 100% $H_2O_2$), relative to the total weight of the agent in each case.

Potassium peroxodisulfate is also referred to as potassium persulfate and has the empirical formula $K_2S_2O_8$.

Ammonium peroxodisulfate is also referred to as potassium persulfate and has the empirical formula $(NH_4)_2S_2O_8$.

Sodium peroxodisulfate is also referred to as potassium persulfate and has the empirical formula $Na_2S_2O_8$.

The persulfate(s) are preferably used in a total quantity of from about 1.0 to about 40.0 wt. % %, such as from about 5.0 to about 30.0 wt. %, for example from about 10.0 to about 25 wt. % and in one embodiment from about 15.0 to about 20.0 wt. %, wherein the aforementioned quantity data refer to the total quantity of all persulfates used in the agent, which is made relative to the total weight of the agent.

A suitable blonding effect can be achieved with the agents which, in addition to hydrogen peroxide, contain at least one persulfate salt. In these agents, the use of the carboxylic acid derivatives of the formula (I) as contemplated herein have proven to be useful.

In a further embodiment, an agent for lightening keratin fibers as contemplated herein is exemplified in that it contains—relative to the total weight of the agent—
(b1) hydrogen peroxide in a quantity of from about 1.0 to about 10.0 wt. %, such as from about 3.0 to about 8.0 wt. % and
(b2) one or more persulfates in a total quantity of from about 10.0 to about 25 wt. %, such as from about 15.0 to about 20.0 wt. %.

In other words, an agent for lightening keratin fibers, more particularly human hair, is most preferred to contain in a cosmetic carrier—relative to the total weight of the agent in each case—
(a) at least one carboxylic acid ester of the formula (I), which is selected from the group of methyl prop-2-enoate, ethyl prop-2-enoate, propyl prop-2-enoate, phenyl prop-2-enoate, methyl 2-methylprop-2-enoate, ethyl 2-methylprop-2-enoate, propyl 2-methylprop-2- enoate, phenyl 2-methylprop-2-enoate, methyl (E)-2-butenoate, ethyl (E)-2-butenoate, propyl (E)-2phenyl (E)-2-butenoate, methyl 3-methyl-2-butenoate, ethyl 3-methyl-2-butenoate, propyl 3-methyl-2-butenoate, phenyl 3-methyl-2-butenoate, methyl (E)-2-methyl-2-butenoate, ethyl (E)-2-methyl-2-butenoate, propyl (E)-2-methyl-2-butenoate, phenyl (E)-2-methyl-2-butenoate, methyl (Z)-2-methyl-2-butenoate, ethyl (Z)-2-methyl-2-butenoate, propyl (Z)-2-methyl-2-butenoate, phenyl (Z)-2-methyl-2-butenoate, methyl 2,3-dimethyl-2-butenoate, ethyl 2,3-dimethyl-2-butenoate, propyl 2,3-dimethyl-2-butenoate, phenyl 2,3-dimethyl-2-butenoate, methyl 2-methylbutanoate, ethyl 2-methylbutanoate, propyl 2-methylbutanoate, phenyl 2-methylbutanoate, methyl (E)-2-pentenoate, ethyl (E)-2-pentenoate, phenyl (E)-2-pentenoate, methyl (E)-3-methyl-2-pentenoate, ethyl (E)-3-methyl-2-pentenoate, phenyl (E)-3-methyl-2-pentenoate, methyl (E)-2-ethyl-2-butenoate, ethyl (E)-2-ethyl-2-butenoate, phenyl (E)-2-ethyl-2-butenoate, methyl (E)-2,3-dimethyl-2-pentenoate, ethyl (E)-2,3-dimethyl-2-pentenoate, phenyl (E)-2,3-dimethyl-2-pentenoate, methyl-2-ethyl-3-methyl-2-butenoate, ethyl-2-ethyl-3-methyl-2-butenoate and/or phenyl-2-ethyl-3-methyl-2-butenoate, and (b1) hydrogen peroxide in a quantity of from about 1.0 to about 10.0 wt. % and (b2) one or more persulfates in a total quantity of from about 10.0 to about 25 wt. % and (c) water, wherein the agent has a pH value in the range of from about 7.5 to about 12.5.

In other words, an agent for lightening keratin fibers, more particularly human hair, is most preferred to contain in a cosmetic carrier—relative to the total weight of the agent in each case—

(a) at least one carboxylic acid ester of the formula (I), which is selected from the group of methyl prop-2-enoate, ethyl prop-2-enoate, propyl prop-2-enoate, phenyl prop-2-enoate, methyl 2-methylprop-2-enoate, ethyl 2-methylprop-2-enoate, propyl 2-methylprop-2-enoate, phenyl 2-methylprop-2-enoate, methyl (E)-2-butenoate, ethyl (E)-2-butenoate, propyl (E)-2-butenoate, phenyl (E)-2-butenoate, methyl 3-methyl-2-butenoate, ethyl 3-methyl-2-butenoate, propyl 3-methyl-2-butenoate, phenyl 3-methyl-2-butenoate, methyl (E)-2-methyl-2-butenoate, ethyl (E)-2-methyl-2-butenoate, propyl (E)-2-methyl-2-butenoate, phenyl (E)-2-methyl-2-butenoate, methyl (Z)-2-methyl-2-butenoate, ethyl (Z)-2-methyl-2-butenoate, propyl (Z)-2-methyl-2-butenoate, phenyl (Z)-2-methyl-2-butenoate, methyl 2,3-dimethyl-2-butenoate, ethyl 2,3-dimethyl-2-butenoate, propyl 2,3-dimethyl-2-butenoate, phenyl 2,3-dimethyl-2-butenoate, methyl 2-methylbutanoate, ethyl 2-methylbutanoate, propyl 2-methylbutanoate, phenyl 2-methylbutanoate, methyl (E)-2-pentenoate, ethyl (E)-2-pentenoate, phenyl (E)-2-pentenoate, methyl (E)-3-methyl-2-pentenoate, ethyl (E)-3-methyl-2-pentenoate, phenyl (E)-3-methyl-2-pentenoate, methyl (E)-2-ethyl-2-butenoate, ethyl (E)-2-ethyl-2-butenoate, phenyl (E)-2-ethyl-2-butenoate, methyl (E)-2,3-dimethyl-2-pentenoate, ethyl (E)-2,3-dimethyl-2-pentenoate, phenyl (E)-2,3-dimethyl-2-pentenoate, methyl-2-ethyl-3-methyl-2-butenoate, ethyl-2-ethyl-3-methyl-2-butenoate and/or phenyl-2-ethyl-3-methyl-2-butenoate, and (b1) hydrogen peroxide in a quantity of from about 3.0 to about 8.0 wt. % and (b2) one or more persulfates in a total quantity of from about 15.0 to about 20.0 wt. %, and (c) water, wherein the agent has a pH value in the range of from about 7.5 to about 12.5.

During the work that led to this disclosure, it emerged that using the carboxylic acid ester(s) (a) of the formula (I) and the peroxide compound(s) (b) in optimally matched ratios is particularly advantageous.

For example, the weight ratio (a)/(b) stands at a value of from about 1/20 (i.e. about 1 weight proportion of carboxylic acid ester (I) to about 20 weight proportions of peroxide) to about 1/100, such as from about 1/30 to about 1/90, for example from about 1/40 to about 1/80 and in one embodiment from about 1/50 to about 1/70. Therefore, using the peroxides (b) in a from about 20 to an about 100-times higher weight than the carboxylic acid esters of the formula (I) has proven to be useful.

In a further most preferred embodiment, the agent for lightening keratin fibers as contemplated herein is exemplified in that the weight ratio from (a) all carboxylic acid esters of the formula (I) contained in the agent to (b) all peroxide compounds contained in the agent, i.e. the weight ratio (a)/(b), stands at a value of from about 1/20 to about 1/100, such as from about 1/30 to about 1/90, for example from about 1/40 to about 1/80 and in one embodiment from about 1/50 to about 1/70.

pH Value

The agent for lightening keratin fibers as contemplated herein has an alkali pH value in the range of from about 7.5 to about 12.5. During the work that led to this disclosure, it emerged that the pH value for achieving a suitable lightening effect is a result-effective variable.

It was observed, for example, that a strong blonding effect is achieved by treating the hair with an agent set to a pH value above 8.0, such as above 8.5, for example above 9.0. However, setting pH values above 11.0 may be avoided, in some embodiments, in order to prevent excessive hair damage and also increased skin irritation.

In a further embodiment, an agent for lightening keratin fibers as contemplated herein is exemplified in that it has a pH value in the range of from about 8.0 to about 10.5, such as from about 8.5 to about 10.0 for example from about 9.0 to about 10.0. In other words, an agent for lightening keratin fibers, more particularly human hair, may contain in a cosmetic carrier—relative to the total weight of the agent in each case—

(a) at least one carboxylic acid ester of the formula (I), which is selected from the group of methyl prop-2-enoate, ethyl prop-2-enoate, propyl prop-2-enoate, phenyl prop-2-enoate, methyl 2-methylprop-2-enoate, ethyl 2-methylprop-2-enoate, propyl 2-methylprop-2-enoate, phenyl 2-methylprop-2-enoate, methyl (E)-2-butenoate, ethyl (E)-2-butenoate, propyl (E)-2-butenoate, phenyl (E)-2-butenoate, methyl 3-methyl-2-butenoate, ethyl 3-methyl-2-butenoate, propyl 3-methyl-2-butenoate, phenyl 3-methyl-2-butenoate, methyl (E)-2-methyl-2-butenoate, ethyl (E)-2-methyl-2-butenoate, propyl (E)-2-methyl-2-butenoate, phenyl (E)-2-methyl-2-butenoate, methyl (Z)-2-methyl-2-butenoate, ethyl (Z)-2-methyl-2-butenoate, propyl (Z)-2-methyl-2-butenoate, phenyl (Z)-2-methyl-2-butenoate, methyl 2,3-dimethyl-2-butenoate, ethyl 2,3-dimethyl-2-butenoate, propyl 2,3-dimethyl-2-butenoate, phenyl 2,3-dimethyl-2-butenoate, methyl 2-methylbutanoate, ethyl 2-methylbutanoate, propyl 2-methylbutanoate, phenyl 2-methylbutanoate, methyl (E)-2-pentenoate, ethyl (E)-2-pentenoate, phenyl (E)-2-pentenoate, methyl (E)-3-methyl-2-pentenoate, ethyl (E)-3-methyl-2-pentenoate, phenyl (E)-3-methyl-2-pentenoate, methyl (E)-2-ethyl-2-butenoate, ethyl (E)-2-ethyl-2-butenoate, phenyl (E)-2-ethyl-2-butenoate, methyl (E)-2,3-dimethyl-2-pentenoate, ethyl (E)-2,3-dimethyl-2-pentenoate, phenyl (E)-2,3-dimethyl-2-pentenoate, methyl-2-ethyl-3-methyl-2-butenoate, ethyl-2-ethyl-3-methyl-2-butenoate and/or phenyl-2-ethyl-3-methyl-2-butenoate, and (b1) hydrogen peroxide in a quantity of from about 1.0 to about 10.0 wt. % and (b2) one or more persulfates in a total quantity of from about 10.0 to about 25 wt. % and (c) water, wherein the agent has a pH value in the range of from about 8.5 to about 10.0.

In other words, an agent for lightening keratin fibers, more particularly human hair, may contain in a cosmetic carrier—relative to the total weight of the agent in each case—

(a) at least one carboxylic acid ester of the formula (I), which is selected from the group of methyl prop-2-enoate, ethyl prop-2-enoate, propyl prop-2-enoate, phenyl prop-2-enoate, methyl 2-methylprop-2-enoate, ethyl 2-methylprop-2-enoate, propyl 2-methylprop-2-enoate, phenyl 2-methylprop-2-enoate, methyl (E)-2-butenoate, ethyl (E)-2-butenoate, propyl (E)-2-butenoate, phenyl (E)-2-butenoate, methyl 3-methyl-2-butenoate, ethyl 3-methyl-2-butenoate, propyl 3-methyl-2-butenoate, phenyl 3-methyl-2-butenoate, methyl (E)-2-methyl-2-butenoate, ethyl (E)-2-methyl-2-butenoate, propyl (E)-2-methyl-2-butenoate, phenyl (E)-2-methyl-2-butenoate, methyl (Z)-2-methyl-2-butenoate, ethyl (Z)-2-methyl-2-butenoate, propyl (Z)-2-methyl-2-butenoate, phenyl (Z)-2-methyl-2-butenoate, methyl 2,3-dimethyl-2-butenoate, ethyl 2,3-dimethyl-2-butenoate, propyl 2,3-dimethyl-2-butenoate, phenyl 2,3-dimethyl-2-butenoate, methyl 2-methylbutanoate, ethyl 2-methylbutanoate, propyl 2-methylbutanoate, phenyl 2-methylbutanoate, methyl (E)-2-pentenoate, ethyl (E)-2-pentenoate, phenyl (E)-2-pentenoate, methyl (E)-3-methyl-2-pentenoate, ethyl (E)-3-methyl-2-pentenoate, phenyl (E)-3-methyl-2-pentenoate, methyl (E)-2-ethyl-2-butenoate, ethyl (E)-2-ethyl-2-butenoate, phenyl (E)-2-ethyl-2-butenoate, methyl (E)-2,3-dimethyl-2-pentenoate, ethyl (E)-2,3-dimethyl-2-pentenoate, phenyl (E)-2,3-dimethyl-2-pentenoate, methyl-2-ethyl-3-methyl-2-butenoate, ethyl-2-ethyl-3-methyl-2-butenoate and/or phenyl-2-ethyl-3-methyl-2-butenoate, and (b1) hydrogen peroxide in a quantity of from about 3.0 to about 8.0 wt. % and (b2) one or more persulfates in a total quantity of from about 15.0 to about 20.0 wt. %, and (c) water, wherein the agent has a pH value in the range of from about 9.0 to about 10.0.

The pH value can be measured by employing a gas electrode, for example, which is commercially available in the form of a combination electrode. Before the pH value is measured, the gas electrodes are calibrated with calibration solutions of a known pH value. The pH values as defined by the present disclosure are pH values that were measured at a temperature of 22° C.

The pH value for this disclosure can be set by employing various alkalizing agents. Suitable alkalizing agents as contemplated herein are selected from the group of ammonia, alkanolamines, alkali metal hydroxides, alkali metal metasilicates, alkali metal phosphates and alkali metal hydrogen phosphates. Preferred inorganic alkalizing agents are sodium hydroxide, sodium hydroxide, sodium silicate and sodium metasilicate. Organic alkalizing agents usable as contemplated herein are selected from monoethanolamine, 2-amino-2-methylpropanol and triethanolamine. Sodium silicate and sodium metasilicate are employed in embodiments.

In a further embodiment, an agent for lightening keratin fibers as contemplated herein is exemplified in that it contains sodium silicate and/or sodium metasilicate as the alkalizing agent.

Sodium silicates are the sodium salts of various silica. A distinction can be drawn between sodium silicates with a ratio of silicon dioxide to sodium monoxide that is equal to 2 or smaller than 1. The latter group includes sodium metasilicate, i.e. sodium metasilicates are polymer silicates of the formula $[Na_2SiO_3]_x$. Sodium metasilicate can be used in its anhydrous form or in the form of its hydrates.

Moreover, sodium silicate can also be used in the form of sodium water glass. Sodium water glass is an amorphous sodium silicate solidified from a melt.

For example, sodium water glass (also referred to as natron water glass) is commercially available from BASF and bears the CAS number 1344-09-8. The raw material is sold in the form of an anhydrous solution with a $SiO_2$ content of approx. 29 wt. % and a $Na_2O$-content of approx. 9 wt. %.

Although the hair treatment agents as contemplated herein are set to pH values in the alkali range, it may be desirable to also use small quantities of acidification agents in order to finely adjust the pH value. Acidification agents as contemplated herein include citric acid, lactic acid, acetic acid and diluted mineral acids (such as hydrochloric acid, sulfuric acid, phosphoric acid).

Kit-of-Parts

To carry out the blonding and/or lightening process described above, the use finds it convenient if all the components for this purpose are provided in the form of a kit-of-parts.

A second subject matter of the present disclosure, therefore, is a kit-of-parts for lightening keratin fibers, packed separately from one another, including:

a container (i) containing an anhydrous cosmetic agent (A), and a container (ii) containing an anhydrous cosmetic agent (B), wherein agent (A) contains hydrogen peroxide, and agent (B) contains at least one persulfate and at least one carboxylic acid ester of the formula (I), wherein the carboxylic acid ester has been disclosed in detail in the description of the first subject matter of this disclosure, and wherein the mixture of agents (A) and (B) has a pH value in the range of from about 7.5 to about 12.5.

In other words, the second subject matter of the present disclosure is a kit-of-parts for lightening keratin fibers, packed separately from one another, including a container (i) containing an anhydrous cosmetic agent (A), and a container (ii) containing an anhydrous cosmetic agent (B), wherein agent (A) contains hydrogen peroxide, and agent (B) contains at least one persulfate and at least one carboxylic acid ester of the formula (I),

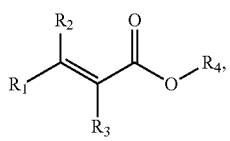

(I)

wherein $R_1$, $R_2$, $R_3$ denote independently a hydrogen atom, a $C_1$-$C_6$-alkyl group, a $C_2$-$C_6$-alkenyl group, a hydroxy-$C_1$-$C_6$-alkyl group, or a $C_1$-$C_6$-alkoxy carbonyl group, $R_4$ denotes a $C_1$-$C_6$-alkyl group, a $C_2$-$C_6$-alkenyl group or an aryl group, and wherein the mixture of agents (A) and (B) has a pH value in the range of from about 7.5 to about 12.5.

Agent (A) contains water and hydrogen peroxide. In one embodiment, the water content of agent (A)—relative to the total weight of agent (A)—is from about 50 to about 90 wt. %

As contemplated herein, agent (B) is anhydrous. As used in the present disclosure, anhydrous means that the water content in agent (B)—relative to the total weight of agent (B)—is a maximum of about 5.0 wt. %, such as about 1.0 wt. % for example a maximum of about 0.1 wt. %.

The anhydrous agent (B) contains, in addition to at least one persulfate (which can alternatively be referred to as peroxodisulfate), at least one carboxylic acid ester of the formula (I).

To produce the ready-for-use agent, agents (A) and (B) are mixed together. The mixing ratio in which agents (A) and (B) are mixed together is from about 1:5 to about 5:1, such as from about 1:3 to about 3:1, for example from about 2:1 to about 1:2.

For example:

100 g of agent (A) are mixed with 50 g of agent (B),
100 g of agent (A) are mixed with 100 g of agent (B), or
50 g of agent (A) are mixed with 100 g of agent (B).

The pH value of the mixture from agents (A) and (B) is in the range of from about 7.5 to about 12.5, such as in the range of from about 8.0 to about 10.5, for example from about 8.5 to about 10.0 and in one embodiment from about 9.0 to about 10.0.

Moreover, it has emerged that providing anhydrous agent (B) in the form of a paste or cream is useful in some embodiments. For this purpose, agent (B) contains—relative to the total weight of agent (B)—one or more fatty constituents in a total quantity of at least about 20 wt. %. One embodiment is for agent (B)—relative to the total weight of agent (B)—to contain one or more fatty constituents in a total quantity of at least about 30 wt. %.

To the extent required by the invention, "fatty constituents" are organic compounds with a water solubility at room temperature (22° C.) and atmospheric pressure (760 mmHg) of less than about 1 wt. %, such as less than about 0.1 wt.-%. The definition of fatty constituents explicitly includes only uncharged (i.e. non-ionic) compounds. Fatty constituents have at least one saturated or unsaturated alkyl group with at least 8 C-atoms. The molecular weight of the fatty constituents is a maximum of about 5000 g/mol, such as a maximum of about 2500 g/mol and in one embodiment a maximum of about 1000 g/mol. The fatty constituents are neither polyoxyalkylated nor polyglycerylated compounds.

Exemplary fatty constituents in this context are the constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. The present disclosure explicitly considers only non-ionic substances to be fatty constituents. Charged compounds such as fatty acids and their salts are not considered to be fatty constituents.

The $C_{12}$-$C_{30}$ fatty alcohols can be saturated, mono- or poly-unsaturated, linear or branched fatty alcohols with 12 to 30 C-atoms.

Examples of linear, saturated $C_{12}$-$C_{30}$ fatty alcohols are dodecan-1-ol (dodecylalcohol, laurylalcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidon alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

Exemplary branched fatty alcohols are 2-octyl-dodecanol, 2-hexyl-dodecanol and/oder 2-butyl-dodecanol.

As used in the present disclosure, a $C_{12}$-$C_{30}$ fatty acid triglyceride is the triester of the trivalent alcohol glycerin with three equivalent fatty acids. Both identically structured and different fatty acids within a triglyceride molecule can be involved in the ester formation.

As used in the present disclosure, fatty acids are saturated or unsaturated, unbranched or branched, unsubstituted or substituted $C_{12}$-$C_{30}$ carboxylic acids. Unsaturated fatty acids can be unsaturated or polyunsaturated. The C—C double bond(s) of an unsaturated fatty acid can have the cis- or trans configuration.

Fatty acid triglycerides are characterized by their particular suitability, for which at least one of the ester groups, based on glycerine, is formed with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidinic acid [(9E)-octadec-9-enic acid], eruca acid [(13Z)-docos-13-enic acid], linoleic acid [(9Z, 12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-trienoic acid] and/or nervonic acid [(15Z)-tetracos-15-enic acid].

The fatty acid triglycerides can also be from natural sources. The fatty acid triglycerides occurring in soy bean oil, peanut oil, sunflower oil, macadamia nut oil, drumstick tree oil, apricot kernel oil, marula oil and/or possibly hardened caster oil, and the mixtures thereof are suitable for use in the product as contemplated herein.

A $C_{12}$-$C_{30}$ fatty acid monoglyceride is the monoester of the trivalent alcohol glycerine with an equivalent fatty acid. Either the middle hydroxy group of the glycerin or the final hydroxy group of the glycerin can be esterified with the fatty acid.

The $C_{12}$-$C_{30}$ fatty acid triglycerides are characterized by their particular suitability, for which at least one hydroxy group of the glycerin is esterified, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidinic acid [(9E)-octadec-9-enic acid], *eruca* acid [(13Z)-docos-13-enic acid], linoleic acid [(9Z, 12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-trienoic acid] and/or nervonic acid [(15Z)-tetracos-15-enic acid].

A $C_{12}$-$C_{30}$ fatty acid diglyceride is the diester of the trivalent alcohol glycerin with two equivalent fatty acids. Either the middle and a terminal hydroxy group of the glycerin can be esterified with two equivalents of fatty acid or both terminal hydroxy groups of the glycerin are each esterified with one fatty acid. The glycerin can be esterified with two identically structured or two different fatty acids.

Fatty acid diglycerides are characterized by their suitability, for which at least one of the ester groups, based on glycerin, is formed with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidinic acid [(9E)-octadec-9-enic acid], *eruca* acid [(13Z)-docos-13-enic acid], linoleic acid [(9Z, 12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-trienoic acid] and/or nervonic acid [(15Z)-tetracos-15-enic acid].

Hydrocarbons are compounds including only the atoms hydrocarbon and hydrogen with from 8 to about 80 C-atoms. In this context, aliphatic hydrocarbons such as mineral oils, liquid paraffin oils (e.g. paraffinum liquidum or paraffinum perliquidum), isoparaffin oils, semi-solid paraffin oils, paraffin waxes, hard paraffin (paraffinum solidum), vaseline and polydecene are exemplary.

In this context, liquid paraffin oils (paraffinum liquidum and paraffinum perliquidum) have proven to be suitable. An exemplary hydrocarbon is paraffinum liquidum, also referred to as white oil. Paraffinum liquidum is a mixture of cleaned, saturated, aliphatic hydrocarbons, which include mainly hydrogen chains with a C-chain distribution from 25 to 35 C-atoms.

In another embodiment, a kit-of-parts is accordingly exemplified in that agent (B)—relative to the total weight of agent (B)—contains one or more fatty constituents in a total quantity of at least about 20 wt. %, wherein the fatty constituents are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In another embodiment, a kit-of-parts is accordingly exemplified in that agent (B)—relative to the total weight of agent (B)—contains one or more fatty constituents in a total quantity of at least about 30 wt. %, wherein the fatty constituents are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

With respect to particular embodiments of the kit-of-parts as contemplated herein, the agents mentioned in the present disclosure apply mutatis mutandis.

Other Constituents

The agents as contemplated herein (and/or agents (A) and (B) of the kit-of-parts) can also contain other active substances, excipients and additional components, such as cationic surfactants, non-ionic surfactants, amphoteric and/or zwitterionic surfactants, anionic surfactants, anionic, non-ionic and/or cationic polymers, structurants such as glucose, perfume oils, fiber structure-improving active substances, more particularly mono-, di- and oligosaccharides such as glucose, galactose, fructose, laevulose and lactose; dyes for coloring the agent: anti-dandruff substances such as piroctone olamine, zinc omadine and climbazole; amino acids and oligopeptides; animal and/or plant-based hydrolyzed proteins, and also in the form of their fatty acid condensation products or possible anionically or cationically modified derivatives; vegetable oils; light stabilizers and UV blockers; active ingredients such as panthenol, pantothenic acid, pantolacton, allantoin, pyrrolidinon carboxylic acids and their color-changing salts, as well bisabolol; polyphenols, more particularly hydroxycinnamic acids, 6,7-dihydroxycumarine, hydroxybenzoic acids, catechines, tannins, leucoanthocyanidins, anthocyanidins, flavanons, flavons and flavonols; vitamins, provitamins and vitamin precursors; plant extracts; source and penetration substances such as glycerin, propylene glycol monoethyl ether, carbonates, hydrogen carbonates, guanidines, ureas, as well as primary, secondary and tertiary phosphates; pacifiers such as latex, styrene/PVP- and styrene/acrylamide copolymers; pearl-shine agents such as ethylene glycol mono- and -distearate as well as PEG-3-distearate; pigments and propellants such as propane-butane mixtures, $N_2O$, dimethyl ether, $CO_2$ and air.

In the agents as contemplated herein, each of the additional active substances and excipients are used in quantities of from about 0.0001 to about 10 wt. %, for example from about 0.0005 to about 5 wt. %, relative to the total weight of agent (A) and/or the peroxide compound preparation (B).

Dyes

Insofar as the agent as contemplated herein is an agent for coloring blonding (i.e. for tinting the blonding effect), the agent can also contain small quantities of at least one oxidizing dye precursor and/or at least one partially-oxidizing dye.

Oxidative dyes are produced with oxidizing dye precursors on the basis of developer and coupler components on the keratin fiber. Oxidizing dye precursors of the developer type include p-phenylendiamine, p-toluylendiamine, N,N-bis-(β-hydroxyethyl)-p-phenylendiamine, 4-N,N-bis-(β-hydroxyethyl)-amino-2-methylaniline, 2-(β-hydroxyethyl)-p-phenylendiamine, 2-(α,β-dihydroxyethyl)-p-phenylendiamine, 2-hydroxymethyl-p-phenylendiamine, bis-(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/or 4,5-diamino-1-(β-hydroxyethyl)-pyrazol.

Oxidizing dye precursors of the coupler type include m-phenylendiamine derivatives, naphthols, resorcinol and resorcinol derivatives, pyrazolones and m-aminophenol derivatives. Particularly suitable coupler substances are 1-naphthol, 1,5-, 2,7- and 1,7-dihydroxy naphthaline, 5-amino-2-methylphenol, m-aminophenol, resorcinol, resorcinol monomethyl ether, m-phenylendiamine, 1-phenyl-3-methyl-pyrazolone-5, 2,4-dichloro-3-aminophenol, 1,3-bis- (2',4'-diaminophenoxy)-propane, 2-chloro-resorcinol, 4-chloro-resorcinol, 2-chloro-6-methyl-3-aminophenol, 2-amino-3-hydroxypyridine, 2-methylresorcinol, 5-methylresorcinol and 2-methyl-4-chloro-5-aminophenol, 1-naphthol, 1,5-dihydroxynaphthaline, 2,7-dihydroxynaphthaline, 1,7-dihydroxynaphthaline, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

The dyes used in step (I) of the method can also contain one or more partially-oxidizing dyes. Nitrophenylendiamines, nitroaminophenols, azo dyes, anthrachinones or indophenoles are particularly suitable partially-oxidizing dyes. The preferred partially-oxidizing dyes are the compounds known under the international designations and/or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzol, 2-amino-4-nitrophenol, 1,4-bis-(β-hydroxyethyl)-amino-2-nitrobenzol, 3-nitro-4-(β-hydroxyethyl)-aminophenol, 2-(2'-hydroxyethyl)amino-4,6-dinitrophenol, 1-(2'-hydroxyethyl)amino-4-methyl-2-nitrobenzol, 1-amino-4-(2'-hydroxyethyl)-amino-5-chloro-2-nitrobenzol, 4-amino-3-nitrophenol, 1-(2'-ureidoethyl)amino-4-nitrobenzol, 4-amino-2-nitrodiphenylamine-2'-carboxylic acid, 6-nitro-1,2,3,4-tetrahydrochinoxaline, 2-hydroxy-1,4-naphthochinon, picric acid and the salts thereof, 2-amino-6-chloro-4-nitrophenol, 4-ethylamino-3-nitrobenzoic acid and 2-chloro-6-ethylamino-1-hydroxy-4-nitrobenzol.

Moreover, the substrates to be de-colorized can also be dyed with natural, partially-oxidizing dyes that occur in nature, such as Henna red, Henna neutral, Henna black, chamomile blossoms sandalwood, black tea, Cascara bark, sage, logwood, madder root, *catechu*, cedar and alkanna root.

The aforementioned dyes are preferably used in a total quantity of below about 1.0 wt. %, such as in a total quantity of below about 0.5 wt. % and in one embodiment in a total quantity of below about 0.1 wt. %—relative to the total weight of each agent as contemplated herein.

Examples:
1. Formulations
The following formulations were created (all data in wt. %)
1.1. Formulation with Hydrogen Peroxide (Agent (A))

| Substance (INCI) | OX |
| --- | --- |
| Sodium benzoate | 0.04 |
| Dipicolinic acid | 0.10 |
| Disodium pyrophosphate | 0.10 |
| Potassium hydroxide 50% | 0.19 |
| Propanediol-1,2 | 0.50 |
| HEDP 60% | 0.25 |
| Paraffinum Liquidum | 2.00 |
| Cetearyl Alcohol | 3.60 |
| Ceteareth-20 | 1.20 |
| Hydrogen peroxide 50% | 12.20 |
| Water, demineralized | ad 100 |

1.2. Paste with Carboxylic Acid Esters (I) and Persulfate (Agent B))

| Substance (INCI) | V1 | V2 | V3 | E1 |
| --- | --- | --- | --- | --- |
| Versagel M1600 | 5.00 | 5.00 | 5.00 | 5.00 |
| Lanette N | 7.00 | 7.00 | 7.00 | 7.00 |
| Eumulgin B 5 | 4.00 | 4.00 | 4.00 | 4.00 |
| Xanthan NaTrue | 1.50 | 1.50 | 1.50 | 1.50 |
| Sodium metasilicate (anhydrous) | 6.50 | 6.50 | 6.50 | 6.50 |
| Potassium persulfate | 42.00 | 42.00 | 42.00 | 42.00 |
| L-Serin | 0.20 | 0.20 | 0.20 | 0.20 |
| Perfume | 0.60 | 0.60 | 0.60 | 0.60 |
| Tiglic acid E-2,3-dimethyl acrylic acid | — | 1.50 | — | — |
| Crotonic acid (E)-2-Butylenic acid | — | — | 1.50 | — |
| Crotonic acid methylester (Methyl-(E)-2-butenoate) | — | — | — | 1.50 |
| Paraffinum Liquidum | ad 100 | ad 100 | ad 100 | ad 100 |

Versagel M1600: Paraffinum liquidum (mineral oil), ethylene/propylene/styrene copolymer, butylene/ethylene/styrene copolymer
Lanette N: Cetearyl alcohol, sodium cetearyl sulfate
Eumulgin B 5: Ceteareth-50
Xanthan NaTrue: Xanthan Gum The hydrocarbon peroxide formulation (OX) and the persulfate paste (V1, V2, V3 and/or E1) were mixed in the ratio of 1:1 and applied to 2 strands of hair immediately after mixing (treatment time 30 min at room temperature). The pH value of the application mixture was 9.5. After the treatment time, the strands were rinsed, dried and, after 48 hours, measured by employing Difference Scanning Calorimetry (2 samples per strand).

2. Fiber Stability Measurement

The following fusion points were determined by employing a DSC analysis (Perkin Elmer DSC-7). A precise description of the method can be found in DE 196 173 95 A1, for example. The higher the measured value, the more stable the keratin matrix of the hair.

Hair Stability

| | Reference, untreated strands | OX + V1 | OX + V2 | OX + V3 | OX + E1 |
| --- | --- | --- | --- | --- | --- |
| DSC: Peak Apex Temp. (° C.) | 153.4 | 139.2 | 145.8 | 145.1 | 151.6 |

3. Determination of the Lightening Effect

The lightening effect was determined visually by comparison with a non-treated strand and with the blonded reference strand (OX+V1).

| | OX + V1 | OX + V2 | OX + V3 | OX + E1 |
| --- | --- | --- | --- | --- |
| Lightening effect | ++ | + | + | ++ |

++ good lightening
+ lightening
o no lightening

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for lightening keratin fibers, comprising a cosmetic carrier and:
   (a) at least one carboxylic acid ester of the formula (I)

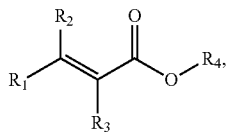

wherein $R_1$ denotes a $C_1$-$C_6$-alkyl group, wherein $R_2$ and $R_3$ denote independently a hydrogen atom, a $C_1$-$C_6$-alkyl group, a $C_2$-$C_6$-alkenyl group, a hydroxy-$C_1$-$C_6$-alkyl group, or a $C_1$-$C_6$-alkoxy carbonyl group, and wherein $R_4$ denotes a $C_1$-$C_6$-alkyl group, a $C_2$-$C_6$-alkenyl group or an aryl group,
   (b) at least one peroxide compound, and
   (c) water.

2. The agent according to claim 1, wherein the agent has a pH value in the range of from 7.5 to 12.5.

3. The agent according to claim 1, wherein $R_2$ denotes a hydrogen atom.

4. The agent according to claim 1, wherein $R_3$ denotes a hydrogen atom.

5. The agent according to claim 1, wherein $R_4$ denotes a methyl group, an ethyl group, a n-propyl group or a n-butyl group.

6. The agent according to claim 1, wherein the (a) at least one carboxylic acid ester of the formula (I) is selected from the group of methyl 2-methylprop-2-enoate, ethyl 2-methylprop-2-enoate, propyl 2-methylprop-2-enoate, phenyl 2-methylprop-2-enoate, methyl (E)-2-butenoate, ethyl (E)-2-butenoate, propyl (E)-2-butenoate, phenyl (E)-2-butenoate, methyl 3-methyl-2-butenoate, ethyl 3-methyl-2-butenoate, propyl 3-methyl-2-butenoate, phenyl 3-methyl-2-butenoate, methyl (E)-2-methyl-2-butenoate, ethyl (E)-2-methyl-2-butenoate, propyl (E)-2-methyl-2-butenoate, phenyl (E)-2-methyl-2-butenoate, methyl (Z)-2-methyl-2-butenoate, ethyl (Z)-2-methyl-2-butenoate, propyl (Z)-2-methyl-2-butenoate, phenyl (Z)-2-methyl-2-butenoate, methyl 2,3-dimethyl-2-butenoate, ethyl 2,3-dimethyl-2-butenoate, propyl 2,3-dimethyl-2-butenoate, phenyl 2,3-dimethyl-2-butenoate, methyl 2-methylbutanoate, ethyl 2-methylbutanoate, propyl 2-methylbutanoate, phenyl 2-methylbutanoate, methyl (E)-2-pentenoate, ethyl (E)-2-pentenoate, phenyl (E)-2-pentenoate, methyl (E)-3-methyl-2-pentenoate, ethyl (E)-3-methyl-2-pentenoate, phenyl (E)-3-methyl-2-pentenoate, methyl (E)-2-ethyl-2-butenoate, ethyl (E)-2-ethyl-2-butenoate, phenyl (E)-2-ethyl-2-butenoate, methyl (E)-2,3-dimethyl-2-pentenoate, ethyl (E)-2,3-dimethyl-2-pentenoate, phenyl (E)-2,3-dimethyl-2-pentenoate, methyl-2-ethyl-3-methyl-2-butenoate, ethyl-2-ethyl-3-methyl-2-butenoate and phenyl-2-ethyl-3-methyl-2-butenoate.

7. The agent according to claim 1, wherein—relative to the total weight thereof—the (a) one or more carboxylic acid esters of the formula (I) is present in a total quantity of from 0.1 to 3.5 wt. %.

8. The agent according to claim 1, wherein the agent comprises as the component (b) at least one peroxide compound from the group of hydrogen peroxide, ammonium peroxodisulfate, potassium persulfate and sodium peroxodisulfate.

9. The agent according to claim 1, wherein the agent comprises as the component (b)—relative to the total weight of the agent—
   (b1) hydrogen peroxide in a quantity of from 1.0 to 10.0 wt. %, and
   (b2) one or more persulfates in a total quantity of from 10.0 to 25.0 wt. %.

10. The agent according to claim 1, wherein a weight ratio from (a) all carboxylic acid esters of the formula (I) contained in the agent to (b) all peroxide compounds contained in the agent (weight ratio (a)/(b)), stands at a value of from 1/20 to 1/100.

11. The agent according to claim 1, wherein the agent has a pH value in the range of from 8.0 to 10.5.

12. The agent according to claim 1, wherein the agent further comprises sodium silicate or sodium metasilicate as an alkalizing agent.

13. A kit-of-parts for lightening keratin fibers, packed separately from one another, and comprising:
   a container (i) comprising an anhydrous cosmetic agent (A), and
   a container (ii) comprising an anhydrous cosmetic agent (B), wherein
   agent (A) comprises hydrogen peroxide, and
   agent (B) comprises at least one persulfate and at least one carboxylic acid ester of the formula (I)

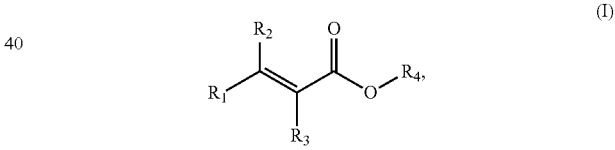

wherein $R_1$ denotes a $C_1$-$C_6$-alkyl group, wherein $R_2$ and $R_3$ denote independently a hydrogen atom, a $C_1$-$C_6$-alkyl group, a $C_2$-$C_6$-alkenyl group, a hydroxy-$C_1$-$C_6$-alkyl group, or a $C_1$-$C_6$-alkoxy carbonyl group, and wherein $R_4$ denotes a $C_1$-$C_6$-alkyl group, a $C_2$-$C_6$-alkenyl group or an aryl group, and
wherein a mixture of agents (A) and (B) has a pH value in the range of from 7.5 to 12.5.

14. The kit-of-parts is according to claim 13, wherein agent (B)—relative to the total weight of agent (B)—comprises one or more fatty constituents in a total quantity of at least 20 wt. %, wherein the one or more fatty constituents are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and hydrocarbons.

15. The kit-of-parts is according to claim 14, wherein agent (B)—relative to the total weight of agent (B)—comprises one or more fatty constituents in a total quantity of at least 30 wt. %.

16. The agent according to claim 1, wherein the keratin fibers comprise human hair.

17. The agent according to claim 1, wherein $R_1$ denotes a methyl group or an ethyl group.

18. The agent according to claim 1, wherein—relative to the total weight thereof—the (a) one or more carboxylic acid esters of the formula (I) is present in a total quantity of from 0.2 to 2.4 wt. %.

19. The agent according to claim 1, wherein—relative to the total weight thereof—the (a) one or more carboxylic acid esters of the formula (I) is present in a total quantity of from 0.4 to 1.2 wt. %.

20. The agent according to claim 1, wherein the agent comprises as the component (b)—relative to the total weight of the agent—
   (b1) hydrogen peroxide in a quantity of from 3.0 to 8.0 wt. %, and
   (b2) one or more persulfates in a total quantity of from 15.0 to 20.0 wt. %.

\* \* \* \* \*